(12) United States Patent
Schick

(10) Patent No.: US 7,448,796 B2
(45) Date of Patent: *Nov. 11, 2008

(54) DIFFERENTIAL SCANNING CALORIMETER (DSC) WITH TEMPERATURE CONTROLLED FURNACE

(75) Inventor: Christoph Schick, Sanitz (DE)

(73) Assignee: PerkinElmer LAS, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/931,163

(22) Filed: Oct. 31, 2007

(65) Prior Publication Data

US 2008/0049810 A1  Feb. 28, 2008

Related U.S. Application Data

(63) Continuation of application No. 11/054,755, filed on Feb. 10, 2005, now Pat. No. 7,371,006.

(60) Provisional application No. 60/521,036, filed on Feb. 10, 2004.

(51) Int. Cl.
    *G01N 25/00* (2006.01)
    *G01K 17/00* (2006.01)
(52) U.S. Cl. .......................................... 374/31; 374/10
(58) Field of Classification Search .................. 374/31, 374/33–34, 10–12
    See application file for complete search history.

(56) References Cited

U.S. PATENT DOCUMENTS

| | | | |
|---|---|---|---|
| 3,263,484 A | 8/1966 | Watson et al. .................. 374/11 |
| 3,319,456 A | 5/1967 | Speros et al. .................. 374/11 |
| 3,667,279 A | 6/1972 | Langer ......................... 374/12 |
| 3,685,344 A | 8/1972 | Karle et al. ................... 374/12 |
| 3,791,202 A | 2/1974 | Vichutinsky et al. .......... 374/12 |
| 4,765,749 A | 8/1988 | Bourgade et al. ............. 374/32 |
| 4,783,174 A | 11/1988 | Gmelin et al. ................ 374/33 |
| 5,288,147 A | 2/1994 | Schaefer et al. .............. 374/10 |
| 5,806,979 A | 9/1998 | Gschneidner, Jr. et al. .... 374/34 |
| 5,813,763 A | 9/1998 | Plotnikov et al. ............. 374/11 |

(Continued)

FOREIGN PATENT DOCUMENTS

EP      0 498 063      8/1992

(Continued)

OTHER PUBLICATIONS

International Search Report and Written Opinion; Jun. 20, 2006; 10 pages.

*Primary Examiner*—Yaritza Gaudalupe-McCall
(74) *Attorney, Agent, or Firm*—St. Onge Steward Johnston & Reens LLC

(57) ABSTRACT

A differential scanning calorimeter apparatus includes reference and sample cells and controlled temperature shields. The temperature of the shields is controlled such that baseline curvature is reduced by eliminating heat flow from the furnaces to their surroundings (quasi adiabatic conditions) and by controlling heat flow through a well defined solid state heat resistance between the furnaces and a temperature controlled heat sink. The temperature of each shield can be controlled independently to reduce differential heat flow over the whole temperature range of the scan, or maintained at a constant temperature for conventional power compensated DSC operation. The temperature/time profile for each shield can be controlled according to actual furnace temperature, obtained from an empty run, or stored in the computer memory and recalled for sample measurements.

20 Claims, 4 Drawing Sheets

U.S. PATENT DOCUMENTS

| | | | |
|---|---|---|---|
| 5,967,659 A | 10/1999 | Plotnikov et al. | 374/11 |
| 5,988,875 A | 11/1999 | Gershfeld et al. | 374/10 |
| 6,238,085 B1 * | 5/2001 | Higashi et al. | 374/10 |
| 6,431,747 B1 | 8/2002 | Danley | 374/10 |
| 6,513,969 B2 * | 2/2003 | Plotnikov et al. | 374/10 |
| 6,523,998 B1 | 2/2003 | Danley et al. | 374/12 |
| 6,530,686 B1 | 3/2003 | Nakamura | 374/11 |
| 6,572,263 B1 | 6/2003 | Refalo et al. | 374/31 |
| 6,641,300 B1 | 11/2003 | Lacey et al. | 374/31 |
| 6,869,214 B2 * | 3/2005 | Plotnikov et al. | 374/31 |
| 6,988,826 B2 | 1/2006 | Zribi et al. | 374/31 |
| 2005/0008063 A1 | 1/2005 | Chippett | 374/34 |

FOREIGN PATENT DOCUMENTS

| | | |
|---|---|---|
| EP | 0 532 480 | 3/1993 |
| EP | 1 351 052 | 10/2003 |
| WO | WO 99/60356 | 11/1999 |

* cited by examiner

DIFFERENTIAL SCANNING CALORIMETER (DSC) WITH TEMPERATURE CONTROLLED FURNACE

CROSS-REFERENCE TO RELATED APPLICATIONS

This application is a continuation of U.S. patent application Ser. No. 11/054,755, filed Feb. 10, 2005 now U.S. Pat. No. 7,371,006, which application is currently pending and which application claims the benefit under 35 U.S.C. §119(e) of the U.S. Provisional Patent Application Ser. No. 60/521,036 filed Feb. 10, 2004 herein incorporated by reference.

FIELD OF THE INVENTION

This invention relates to calorimetric analytical instruments, and more particularly to a temperature controlled shield for differential scanning calorimeter.

BACKGROUND OF THE INVENTION

The differential scanning calorimeter ("DSC") is an apparatus which, when a sample and a reference substance are placed therein, and the temperatures of both are varied at a constant rate, detects and analyzes differentially a heat flow generated or absorbed by the sample as compared with the reference substance.

As the sample material goes through various physical changes, such as fusing, crystallization, freezing, oxidation, and the like, its temperature is affected by the changes in internal energy. The differences in temperature between the sample and the reference are recorded and, from this data, calculations may be made for determining the internal energy changes occurring in the sample. Such information is useful in evaluating materials such as pharmaceuticals, plastics, films and the like.

One type of DSC is power compensation DSC. It is generally structured by a combination of two independent calorimeters for a sample and a reference, and both are provided with a resistance temperature sensor and heat flow feedback heater. The average value of temperatures detected by both temperature sensors is compared with a temperature output of a temperature programmer which varies at a constant rate. Two calorimeters are heated up such that both are brought into coincidence by the heat flow feedback heaters. Also, if a difference is caused in temperature output of the both temperature sensors, both heaters are immediately increased or decreased in power to return the difference to zero. Thereupon, the difference of power supplied to the both heaters is continuously recorded as a differential heat flow signal.

Various power compensated differential scanning calorimeters are known in the art such as U.S. Pat. No. 6,530,686 (herein incorporated by reference) relating to a DSC having low drift and certain response characteristics. The sample temperature is controlled according to a program temperature by a furnace temperature controller, and at the same time controlled by a detector temperature controller. Also, if a temperature difference occurs, the supply powers to heaters separately provided close to the sample and reference are adjusted such that the temperature difference is returned to zero by a differential heat compensating circuit, outputting a difference in supply power as a differential heat flow.

U.S. Pat. No. 3,263,484 (herein incorporated by reference) relates to a method of performing an analysis by changing the temperature of a sample material in accordance with a desired program by varying the temperature of an external medium in heat exchanging relationship with the sample. The difference in temperature between the sample and program is measured and the applied heat is varied to maintain zero temperature difference there between. The power required to maintain the zero temperature differences is then measured.

The power compensation type differential scanning calorimeter is responsive and can quickly realize a heat compensation time constant. However, as for the baseline performance, there has been a difficulty in obtaining stability. The main reason of this lies in that the power compensation type sensor has a large temperature difference from surrounding members during measurement with a result that a comparatively large amount of heat leak occurs from the sensor to the outside, causing a drift factor in the baseline. Moreover, there is operating difficulty and lag time between cycles due to frost formation on the cells during cool down.

SUMMARY OF THE INVENTION

The present methods and systems provide a differential scanning calorimeter comprising at least one cell; at least one thermal shield adjacently positioned to the cell; a heating system capable of heating the cell and the thermal shield; and a temperature monitoring device which monitors a temperature differential between the cell and a reference. In an embodiment, the thermal shield is a cylinder positioned around the cell. The thermal shield can comprise a top end, bottom end, and a sidewall which can have a dielectric layer disposed thereupon. The sidewall can further comprise a perimeter and a groove extending around the perimeter. In an embodiment, the thermal shield further comprises a thermocouple disposed upon the sidewall, and the thermocouple can comprise a thermal resistant wire and a resistive wire. Optionally, the thermal resistant wire is platinum. The thermal shield further can comprise a temperature sensor disposed upon the sidewall. In some embodiments, the thermal shield further comprises a resistive wire disposed upon the sidewall for heating the shield. The thermal shield can be made of high thermal conducting material which may optionally include one or more of aluminum, copper, ceramic, and silver. In an embodiment, the thermal shield is characterized as quasi adiabatic. In one embodiment, the sidewall of the thermal shield is between about 0.25 mm to about 10 mm thick, and for example, can be about 0.5 mm thick. Optionally, at least one first cover can be disposed on the thermal shield. Optionally, a block is positioned around the thermal shield, and optionally, a second cover is disposed upon the block. In some embodiments, there is a gap between the cell and the thermal shield. In one example, the reference is a sample, and optionally, the reference can be data.

The present teachings also include providing a differential scanning calorimeter comprising: a sample cell; a reference cell; a first thermal shield adjacently positioned to the sample cell; a second thermal shield adjacently positioned to the reference cell; a heating system capable of heating the sample cell, the reference cell, the first thermal shield and the second thermal shield; and a temperature monitoring device which monitors a temperature differential between the sample cell and the reference cell. A first heating device can be coupled to the sample cell, a second heating device can be coupled to the reference cell, a third heating device can be coupled to the first thermal shield, and/or a fourth heating device can be coupled to the second thermal shield. Accordingly, one or more heating devices can be coupled to one or more of the sample cell, the reference cell, the first thermal shield, and the second thermal shield. In some embodiments, the differential scanning calorimeter further comprises a control system capable of changing the temperature of the first, second, third, and/or fourth heating devices. Such differential scanning calorimeters can further comprise a computer and/or an output. In an embodiment, the first thermal shield is a cylinder positioned around the sample cell, and the second thermal shield is a cylinder positioned around the reference cell.

The present teachings also include methods of monitoring a temperature differential between the sample cell and the reference comprising: providing a differential scanning calorimeter comprising: sample cell and a reference; at least one thermal shield adjacently positioned to the cells; a heating system capable of heating the cell and the thermal shield; and a temperature monitoring device which monitors a temperature differential between the cell and a reference; obtaining signals from differential scanning calorimeter; and calculating temperature differential between the sample cell and the reference using variables generated by signals. In some embodiments, the methods further comprise using a thermal shield which can be, for example, a cylinder positioned around the cell.

As used herein the term "adiabatic" refers to a process where a system does not exchange heat with the surroundings during the process.

DETAILED DESCRIPTION OF THE INVENTION

Figure 1:
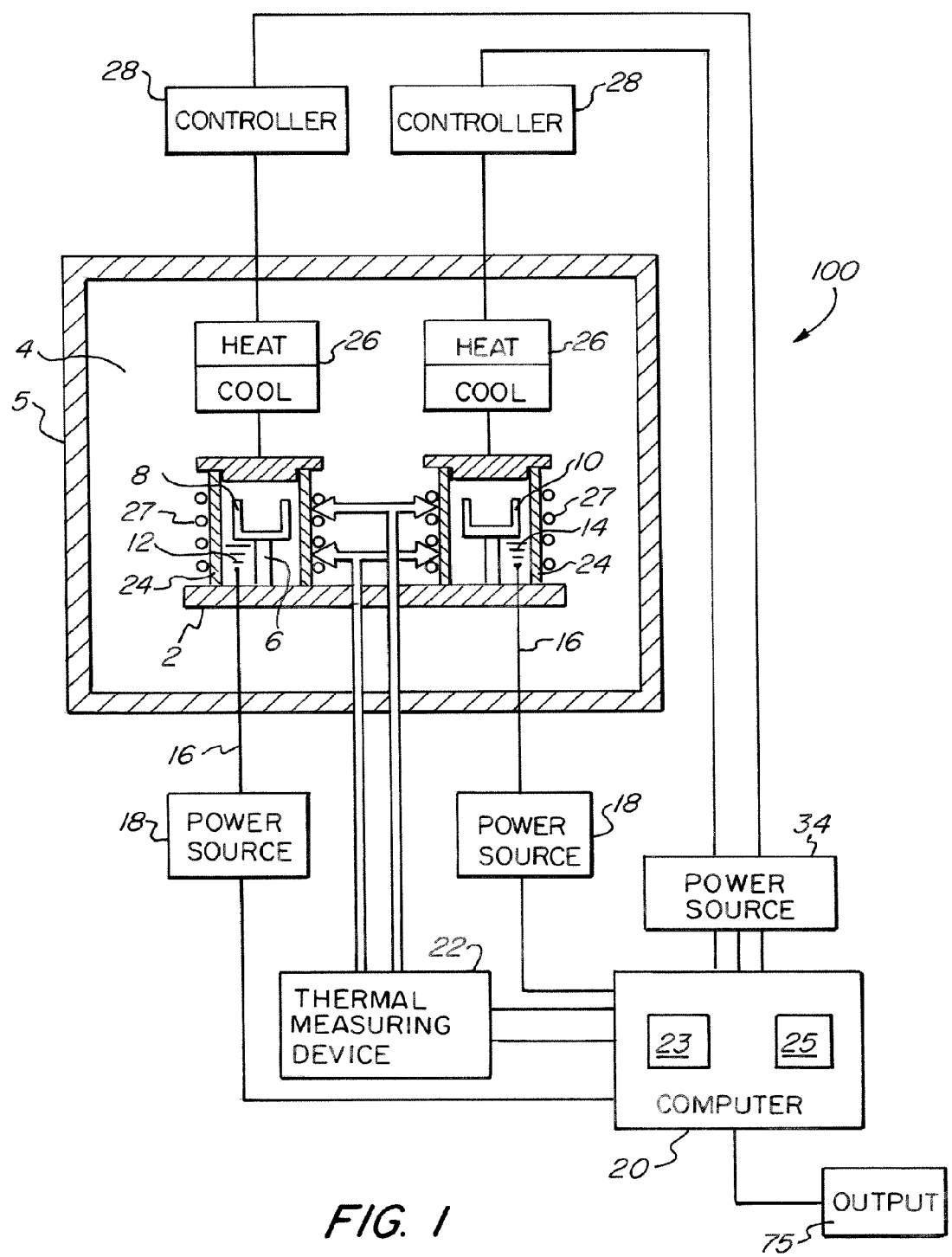
FIG. 1 shows a schematic of a differential scanning calorimeter (DSC) having at least one thermal shield.

A schematic diagram of an embodiment of an improved differential scanning calorimeter (DSC) is shown in FIG. 1. A calorimeter 100 such as PerkinElmer's Diamond DSC may be used to incorporate the present teachings; however, other models may be used such as PerkinElmer's power compensated Pyris 1 DSC, PerkinElmer's DSC 7, or the like. The illustrated DSC has a metal base 2 located in an inner chamber 4 defined by an outer wall 5 which may be a heat shield. Metal base 2 may be connected to a cooling block (not shown in FIG. 1). Support 6 on base 2 holds a reference cell 8 and a sample cell 10, each similar in volume and mass, and assembled with heating elements 12 and 14. Reference cell 8 and sample cell 10 each hold a sample in this case (not shown in FIG. 1), however, one of ordinary skill in the art would appreciate that it is possible to leave reference cell 8 empty, and/or that the reference may be data or a sample which may have known characteristics. Leads 16 connect cells 8 and 10 to a power source 18 to supply power to heating elements 12 and 14 in each of the cells, which may be independently controlled by a processor and/or computer 20. Computer 20 includes an interface 23 so that the user may provide/input specifications, and a memory 25 for storage, for example, a hard drive or random access memory. The illustrated heating elements 12 and 14 are driven by a power source 18, so cells 8 and 10 may be heated at varied or identical rates, which are controlled by the computer 20.

The rate at which the temperature of the cells changes is referred to as the scan rate and can be specified by the user through the computer interface 23. In some embodiments, the scan rate is between 0.01° C. to 500° C./min, although other rates can be specified. As shown, a thermal effect measuring device 22 is connected to a sensor 27 that measures the difference in temperature between the two cells 8, 10. Sensor 27 may be two or more separate sensors capable of independent analysis. In some embodiments, the temperature control of the individual shields 24 is realized by thermal effect measuring device 22 having two independent control loops using a wire such as a platinum wire as thermometer and the resistive wire as heater. One controller measures the average temperature of the two shields and the second controller measures the temperature difference between both shields (as in the measuring portion of the power compensation DSC). In the illustrated embodiment, the average temperatures of the two shields 24 follows a certain function of the temperature of the measuring system (the furnaces) and are operated according to the different modes.

Typical sensors include temperature measuring devices such as wire thermometers, thermocouples or semiconducting thermocouples. The temperature differential is continuously measured as the cells are being heated during a scan. The temperature differential data is then transmitted from thermal effect measuring device 22 to computer 20, where it is saved along with the time of the measurement in the computer memory 25. Output 75 provides data to user such as visual data showing graphs, alphanumeric symbols, and the like.

The cells 8 and 10 are surrounded by a thermal shield 24 which is shown as a cylinder placed around the cells. During adiabatic operation, the thermal shield 24 aids in reducing heat exchange between the cells and their surroundings. The temperature of thermal shield 24 is monitored by thermal effect measuring device 22 and sensors 27 which are mounted on thermal shield 24. Thermal shield 24 is connected to a heating and cooling device 26 which is operated by at least one controller 28. The signal to the controller 28 travels to and from computer 20. The output from cell measuring device 22 is sent to computer 20 and used to determine a signal to transmit to power source 34 and subsequently onto the controller 28. The temperature information is repeatedly stored in the computer memory 35 with the temperature differential between cells and the time of the measurement. For the illustrated embodiments, the operating range for the calorimeter in terms of the temperature at which the cells and shield can be operated is −170° C. to 730° C. The DSC may measure the temperature of thermal shield 24 and cells 8 and 10 with a temperature accuracy of ±0.1° C., and adjust the temperature thereof within the precision of ±0.1° C. Although not shown in FIG. 1, one of ordinary skill in the art would understand that the DSC may be modified with a wide range of DSC accessories and options from StepScan DSC and automatic gas switching to cooling devices and the wide variety of known sample pans.

The illustrated thermal shield 24 is positioned around reference cell 8 and sample cells 10. The power to each of these thermal shields 24 is independently controlled by the output of computer 20. Thermal shield 24 is capable of generating heat, and is used to actively reduce temperature differentials between cells 8 and 10.

The heating system is capable of heating cells 8 or 10 and the thermal shield(s) 24 and may comprise the same or different heating elements defined by a controller. Where one, two, three, four, or more heating elements are used, the heating elements may be commonly controlled or independently controlled by the user.

Through the computer interface 20, the user can select between various operational modes, in which thermal shields 24 are not used or various levels of use in which thermal shields 24 are used by computer 20 to actively minimize the temperature differential between cells 8 and 10.

Modes of operation of the calorimeter having quasi adiabatic thermal shields 24 include:

Mode A: Both thermal shields 24 (sample shield and reference shield) closely follow the furnace program temperature (adiabatic conditions regarding heat exchange through the gas).

Mode B: Both thermal shields 24 (sample shield and reference shield) closely follow the furnace program temperature (adiabatic conditions regarding heat exchange through the gas) as in Mode A but a specified, controlled temperature difference between the thermal shields is introduced to reduce differential heat flow in the measuring system.

Mode C: The temperature of each individual thermal shield 24 (sample shield and reference shield) is controlled separately. To reduce base-line curvature, the temperatures of each shield is adjusted such that for all temperatures the differential heat flow is reduced to, for example, a minimal base-line heat flow. Additionally the heat flow between each furnace and the shield is reduced to a value that can represent quasi-adiabatic conditions. The temperature function for the shield temperatures may be obtained from an empty run and stored as an array or as a smooth function in the computer memory. The temperature function can be recalled during the scan to set the shield's temperatures to minimize base-line heat flow as much as possible.

Mode D: Both shields 24 (sample shield and reference shield) can be operated in a "constant temperature" mode, allowing operation of the DSC in a conventional power compensation mode.

Mode E: To increase heat losses to the surrounding, the shields can be set to the temperature of the heat sink before starting the cooling to increase maximum cooling rate.

Figure 2:
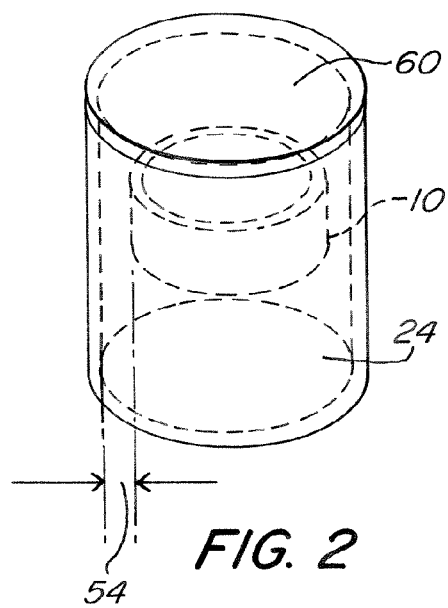
FIG. 2 is a front isometric view of a DSC sub-assembly with a temperature controlled shield such as that shown in FIG. 1.

Referring now to FIG. 2, DSC sub-assembly with a separate temperature controlled shield is shown. The quasi adiabatic temperature controlled shield 24 is shown encompassing a cell, such as sample cell 10. Shield 24 is made of high thermal conducting material such as one or more of aluminum, copper, ceramic or silver to avoid temperature gradients across shield 24. The temperature gradient and the heat losses which are needed to allow fast cooling are defined by the connections (feet) of the shield (not shown in FIG. 2) and the temperature controlled heat sink at the base of the measuring system (not shown in FIG. 2). The connections (feet) are constructed of a metal or ceramic material to allow high temperature operation. Shield 24 comprises a thin walled (between 0.25 mm to 10 mm thick, preferably about 0.5 mm) cylinder. Gap 54 lies between cell 10 and thermal shield 24. In the illustrated embodiment, the gap 54 has a width between 0.25 mm and 10 mm, and in some embodiments between about 0.5 mm to about 1.5 mm and yet in other embodiments about 1.0 mm to promote adiabatic processes. First cover 60 is shown disposed on top of thermal shield 24.

Figures 3A, 3B:
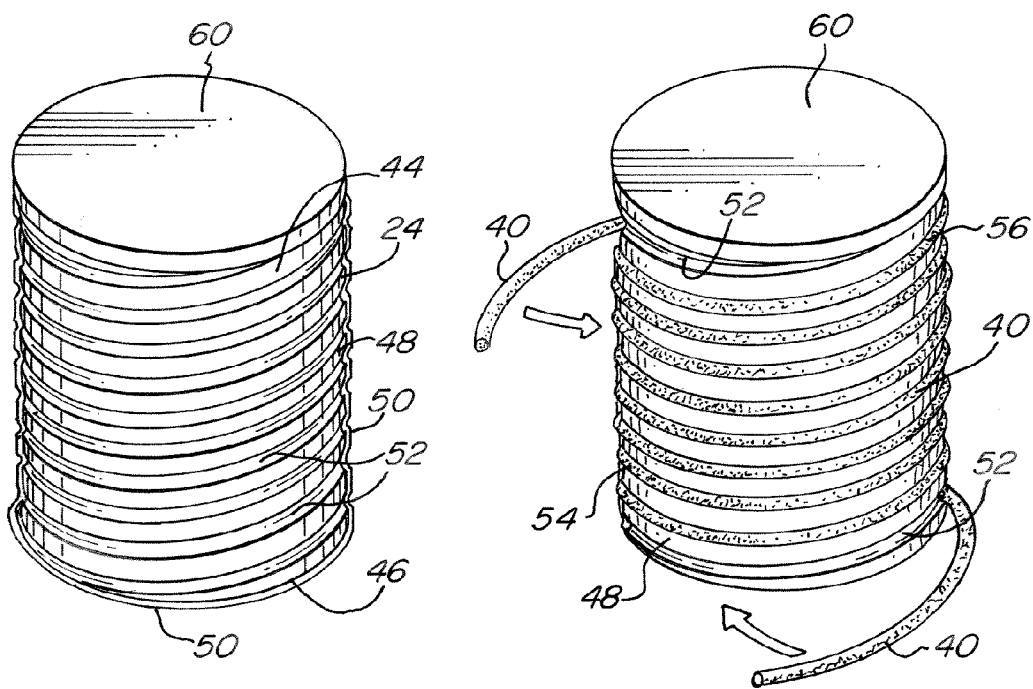
FIG. 3(a) and FIG. 3(b) are side isometric views of a temperature controlled shield such as that shown in FIG. 2.

Referring now to FIG. 3a thermal shield 24 in the shape of a cylinder is shown having top end 44, bottom end 46 and sidewall 48. First cover 60 is shown disposed on top of thermal shield 24. Sidewall 48 is covered with a dielectric layer 50, e.g., a glass or alumina layer, to electrically isolate wires from the cylinder giving a very short response time. Sidewall 48 has an outer perimeter and is threaded, thus groove 52 extends around the outer perimeter. Referring to FIG. 3(b), wire 40 is shown placed within groove 52 extending around the perimeter of thermal shield. In some embodiments, wire 40 may be a thermometer or thermocouple disposed upon the sidewall 48 comprising a temperature resistive wire portion 54 and resistive wire portion 56 as a heater. In some embodiments, wire 40 is capable of acting as a temperature sensor. Both temperature resistive wire 54 and resistive wire 56 are wound around the outside of the cylinder covering a large area of sidewall 48 to realize a short response time for temperature control. To avoid contact between the heater and sensor wires, each is contained in separate parallel grooves and may be fixed in place with high temperature ceramic glue. Thermal resistant wire 54 is can be made of platinum. Although not shown in FIG. 3, in the illustrated embodiment, the platinum wires are connected with gold braze to a platinum connector ribbon providing high temperature operation.

Figure 4A:
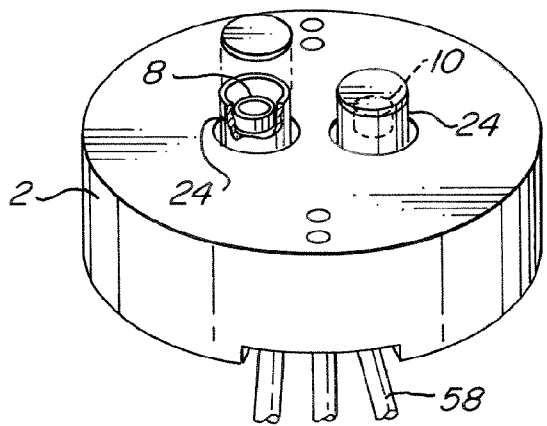
FIG. 4(a) is a front isometric view of a DSC measuring system having two sub-assemblies such as shown in FIG. 2.
Figure 4B:
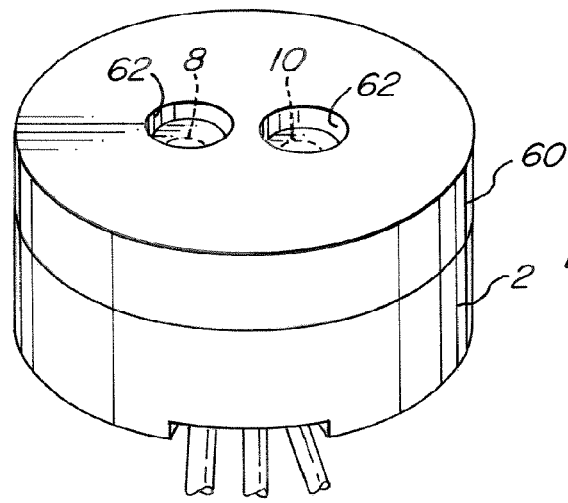
FIG. 4(b) shows measuring system of FIG. 4(a) having a metal block.
Figure 4C:
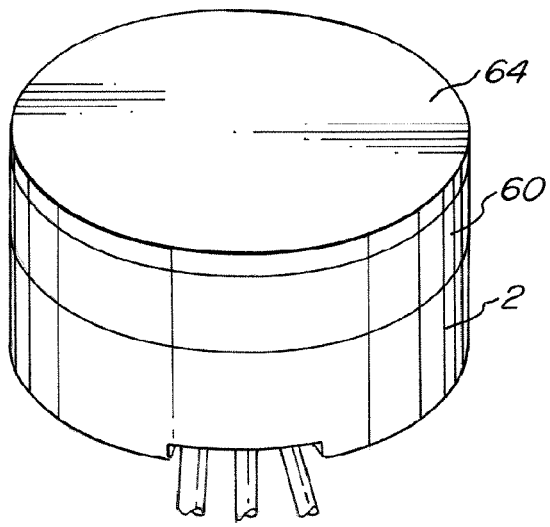
FIG. 4(c) shows measuring system of FIG. 4(b) having an additional cover disposed on block.

Referring to FIG. 4(a), a DSC measuring system is shown having two sub-assemblies comprising a reference cell 8 and a sample cell 10. The subassemblies and circuitry is enclosed in metal base 2. Various leads 58 are shown entering the bottom portion of base 2 which are used to provide signals to and from the computer to the sensors and heaters positioned in the subassemblies (not shown in FIG. 4(a)). Reference cell 8 and sample cell 10 are shown adjacent one another in the center of the apparatus. Thermal shields 24 surround reference cell 8 and sample cell 10 and extend up and out of metal base 2. Referring to FIG. 4(b), a DSC measuring system having the same features as FIG. 4(a) is shown; however, aluminum block 60 is placed upon metal base 12. Metal block 60 can be made of aluminum and contains two openings 62 positioned in the center of the block such that the block may be placed on metal base 2, and snugly surround reference cell 8 and sample cell 10, both having thermal shield 24. FIG. 4(c) shows a second cover 64 placed over block 60 such that openings 62 become covered.

Figure 5:
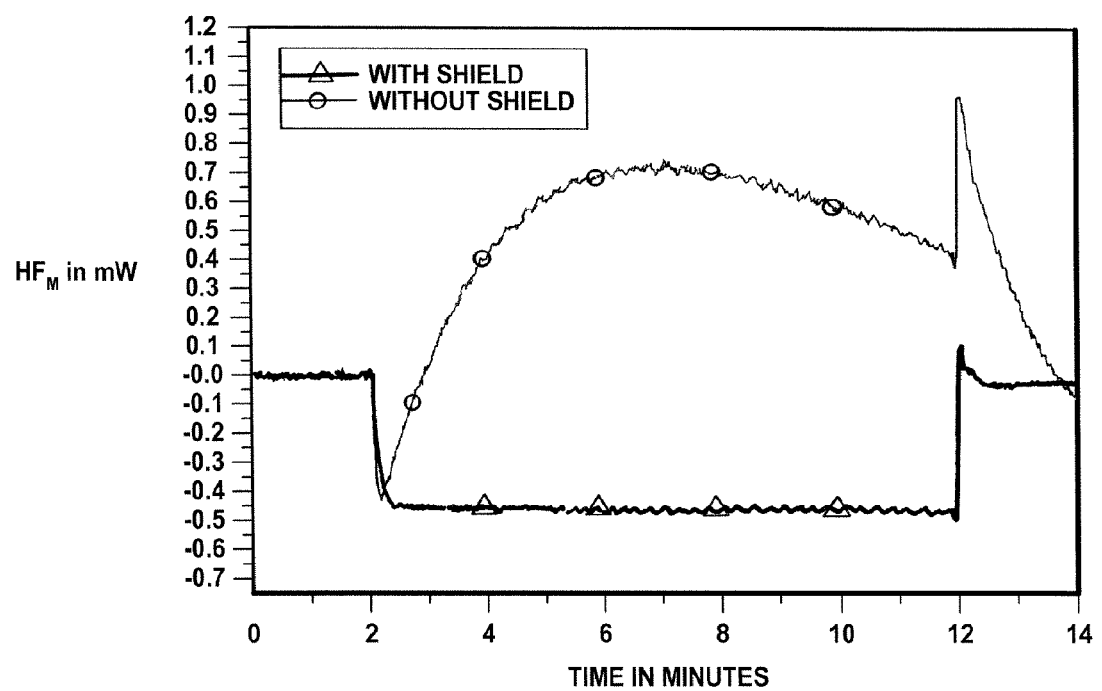
FIG. 5 is a graph of heat flow of an empty measuring system of FIG. 4(c) at 10 K/min heating from 350 K to 450 K.

FIG. 5 shows a graph of heat flow of an empty measuring system at 10 K/min heating from 350 K to 450 K using temperature control shields surrounding reference cell and sample cell. The effect of the quasi adiabatic temperature controlled shield as operated as described herein on base-line straightness can be seen in FIG. 5. The temperature control of the shields improves base-line straightness. In this case, the temperature of the shields closely followed the temperature of the measuring system. One of ordinary skill in the art appreciates that additional advanced control algorithms may be added to improve base-line straightness and noise level even further.

Obviously, many modifications may be made without departing from the basic spirit of the present teachings. Accordingly, it will be appreciated by those skilled in the art that within the scope of the appended claims, the invention may be practiced other than has been specifically described herein.

What is claimed is:

1. A differential scanning calorimeter comprising:
   a first cell and a second cell;
   a first thermal shield corresponding to said first cell and a second thermal shield corresponding to said second cell;
   said first thermal shield is separate from said second thermal shield;
   each of said thermal shields includes a top end, a bottom end, and a sidewall; and
   a processor coupled to a heating system and a temperature monitoring device for controlling heat to each of said cells and each of said thermal shields and for monitoring a temperature differential between said first cell and said second cell.

2. The differential scanning calorimeter of claim 1, wherein said thermal shield is a cylinder positioned around the cell.

3. The differential scanning calorimeter of claim 1, further comprising a gap between each of said cells and its corresponding thermal shield.

4. The differential scanning calorimeter of claim 3, wherein a dielectric layer is disposed upon the sidewall.

5. The differential scanning calorimeter of claim 1, wherein the sidewall further comprises a perimeter and a groove extending around the perimeter.

6. The differential scanning calorimeter of claim 1, wherein each of said thermal shields further comprises a thermocouple disposed upon the sidewall.

7. The differential scanning calorimeter of claim 6, wherein the thermocouple comprises a thermal resistant wire and a resistive wire.

8. The differential scanning calorimeter of claim 7, wherein the thermal resistant wire is platinum.

9. The differential scanning calorimeter of claim 1, wherein each of said thermal shields further comprises a temperature sensor disposed upon the sidewall.

10. The differential scanning calorimeter of claim 1, wherein each of said thermal shields further comprises a resistive wire disposed upon the sidewall for heating said shield.

11. The differential scanning calorimeter of claim 1, wherein the thermal shield is made of high thermal conducting material.

12. The differential scanning calorimeter of claim 11, wherein the high thermal conducting material includes at least one of aluminum, copper, ceramic, and silver.

13. The differential scanning calorimeter of claim 1, wherein each of said thermal shields is characterized as quasi adiabatic.

14. The differential scanning calorimeter of claim 1, wherein the sidewall is between about 0.25 mm to about 10 mm thick.

15. The differential scanning calorimeter of claim 1, wherein the sidewall is 0.5 mm thick.

16. The differential scanning calorimeter of claim 1, further comprising at least one first cover disposed on each of said thermal shield.

17. The differential scanning calorimeter of claim 1, further comprising a block positioned around each of said thermal shields.

18. The differential scanning calorimeter of claim 17, further comprising a second cover disposed upon said block.

19. A differential scanning calorimeter comprising:
   a sample cell;
   a reference cell;
   a first thermal shield adjacently positioned to the sample cell;
   a second thermal shield adjacently positioned to the reference cell and separate from said first thermal shield;
   each of said first and second thermal shields comprises a top end, a bottom end, and a sidewall;
   at least one heating system capable of heating said sample cell, said reference cell, said first thermal shield and said second thermal shield; and
   a temperature monitoring device which monitors a temperature differential between the sample cell and the reference cell.

20. The differential scanning calorimeter of claim 19, wherein the at least one heating system comprises at least one of:
   a first heating device coupled to the sample cell,
   a second heating device coupled to the reference cell,
   a third heating device coupled to the first thermal shield,
   a fourth heating device coupled to the second thermal shield, and
   a control system capable of changing the temperature of at least one of said first, second, third, and fourth heating devices.

* * * * *